(12) United States Patent
Wise

(10) Patent No.: US 9,622,938 B2
(45) Date of Patent: *Apr. 18, 2017

(54) METHOD AND APPARATUS FOR TREATING PELVIC PAIN

(71) Applicant: National Center for Pelvic Pain Research Devices, Inc., San Francisco, CA (US)

(72) Inventor: David Wise, Sebastopol, CA (US)

(73) Assignee: National Center for Pelvis Pain Research Devices, Inc., San Francisco, CA (US)

( * ) Notice: Subject to any disclaimer, the term of this patent is extended or adjusted under 35 U.S.C. 154(b) by 424 days.

This patent is subject to a terminal disclaimer.

(21) Appl. No.: 14/091,882

(22) Filed: Nov. 27, 2013

(65) Prior Publication Data

US 2014/0088469 A1 Mar. 27, 2014

Related U.S. Application Data

(63) Continuation-in-part of application No. 13/723,263, filed on Dec. 21, 2012, now Pat. No. 8,632,482,
(Continued)

(51) Int. Cl.
*A61H 23/00* (2006.01)
*A61H 19/00* (2006.01)
(Continued)

(52) U.S. Cl.
CPC .............. *A61H 23/00* (2013.01); *A61H 19/40* (2013.01); *A61H 21/00* (2013.01);
(Continued)

(58) Field of Classification Search
CPC . A61H 1/00; A61H 7/00; A61H 23/00; A61H 23/0245; A61H 23/0263;
(Continued)

(56) References Cited

U.S. PATENT DOCUMENTS 2,478,786 A 8/1949 Smallen
2,957,474 A 10/1960 Bates et al.
(Continued)

FOREIGN PATENT DOCUMENTS

JP 2004181160 A * 7/2004 ............. A61H 21/00

OTHER PUBLICATIONS

International Search Report and Written Opinion of the International Searching Authority, International Application No. PCT/US2014/067551, Feb. 18, 2015.
(Continued)

*Primary Examiner* — Quang D Thanh
(74) *Attorney, Agent, or Firm* — Young Basile Hanlon & MacFarlane, P.C.

(57) ABSTRACT

A hand-held internal therapeutic massager includes a rod having a first portion that defines a curve and a second portion that is substantially straight. The first portion of the rod is adapted to be inserted into a patient's body. A curvature of the curve defined by the first portion of the rod is sufficient to prevent the second portion of the rod from entering a patient's body. A handle is located on the second portion of the rod and a pressure applicator on the first portion of the rod is adapted to be inserted into the patient's body for engagement with a localized area of myofascial tissue. A vibratory device is disposed within the handle and is operable to generate vibrations. The vibrations generated by the vibratory device are conducted through the rod to the pressure applicator to the localized area of myofascial tissue.

19 Claims, 12 Drawing Sheets

Related U.S. Application Data which is a continuation of application No. 12/115,807, filed on May 6, 2008, now Pat. No. 8,337,435.

(60) Provisional application No. 60/928,033, filed on May 7, 2007.

(51) Int. Cl.
| | | |
|---|---|---|
| *A61N 1/05* | (2006.01) | |
| *A61N 1/36* | (2006.01) | |
| *A61H 21/00* | (2006.01) | |
| *A61H 23/02* | (2006.01) | |
| *A61B 5/03* | (2006.01) | |
| *A61B 5/00* | (2006.01) | |
| *A61H 15/00* | (2006.01) | |

(52) U.S. Cl.
CPC ..... *A61H 23/0245* (2013.01); *A61H 23/0263* (2013.01); *A61N 1/0512* (2013.01); *A61N 1/0524* (2013.01); *A61N 1/36007* (2013.01); *A61B 5/036* (2013.01); *A61B 5/742* (2013.01); *A61B 2560/04* (2013.01); *A61B 2562/0247* (2013.01); *A61B 2562/16* (2013.01); *A61H 2015/0042* (2013.01); *A61H 2201/0173* (2013.01); *A61H 2201/5043* (2013.01); *A61H 2201/5071* (2013.01); *A61N 1/36021* (2013.01)

(58) Field of Classification Search
CPC ........ A61H 19/00; A61H 19/04; A61H 21/00; A61H 2015/0042; A61H 2201/10; A61H 2201/0153; A61H 2201/1628; A61H 2201/5043; A61H 2201/5071; A61H 19/40; A61H 2201/0173; A61N 1/0512; A61N 1/0524; A61N 1/36007; A61N 1/36021; A61B 5/036; A61B 5/742; A61B 2560/04; A61B 2562/16; A61B 2562/0247

See application file for complete search history.

(56) References Cited

U.S. PATENT DOCUMENTS

| | | | |
|---|---|---|---|
| 3,504,665 | A | 4/1970 | Bakunin et al. |
| 3,809,091 | A | 5/1974 | Shute |
| 3,994,301 | A | 11/1976 | Agris |
| 4,002,164 | A | 1/1977 | Bradley |
| 5,224,469 | A | 7/1993 | Mocny |
| 5,291,902 | A | 3/1994 | Carman |
| 5,404,881 | A * | 4/1995 | Cathaud ................ A61B 18/18 600/407 |
| 5,643,311 | A | 7/1997 | Smith et al. |
| 5,690,603 | A | 11/1997 | Kain |
| 5,853,362 | A | 12/1998 | Jacobs |
| 6,063,045 | A | 5/2000 | Wax et al. |
| 6,567,990 | B1 | 5/2003 | Spitznagle |
| 6,741,895 | B1 | 5/2004 | Gafni et al. |
| 6,758,826 | B2 | 7/2004 | Luettgen et al. |
| 7,079,882 | B1 | 7/2006 | Schmidt |
| 7,206,641 | B2 | 4/2007 | Ignagni et al. |
| 7,628,744 | B2 | 12/2009 | Hoffman et al. |
| 7,695,489 | B2 | 4/2010 | Brockman |
| 8,224,464 | B2 * | 7/2012 | Wise ..................... A61H 21/00 600/38 |
| 8,337,435 | B2 | 12/2012 | Wise |
| 8,632,482 | B2 * | 1/2014 | Wise ..................... A61N 1/0512 601/135 |
| 2004/0030360 | A1 | 2/2004 | Eini et al. |
| 2005/0113726 | A1 * | 5/2005 | Prettyman .......... A61H 15/0092 601/119 |
| 2007/0270727 | A1 | 11/2007 | Khorassani Zadeh |
| 2009/0210027 | A1 | 8/2009 | Wise |
| 2011/0190574 | A1 | 8/2011 | Maurette |

OTHER PUBLICATIONS

United States Patent and Trademark Office, Non-Final Office Action dated Nov. 23, 2011, U.S. Appl. No. 12/115,807.

United States Patent and Trademark Office, Non-Final Office Action dated Jul. 30, 2012, U.S. Appl. No. 12/115,807.

\* cited by examiner

METHOD AND APPARATUS FOR TREATING PELVIC PAIN

CROSS-REFERENCE TO RELATED APPLICATIONS

This application is a continuation-in-part of U.S. patent application Ser. No. 13/723,263, filed Dec. 21, 2012, now U.S. Pat. No. 8,632,482, which is a continuation of U.S. patent application Ser. No. 12/115,807, filed May 6, 2008, which claims the benefit of U.S. Provisional Patent Application No. 60/928,033, filed May 7, 2007.

FIELD OF THE INVENTION

The present invention relates to a method and apparatus for treating pelvic pain in women and men.

BACKGROUND OF THE INVENTION

Pelvic pain has long been a problem among women and men. Conventional medicine has treated pelvic pain in various ways including, 1) an organ-specific focus in which pelvic pain is believed to be a symptom of inflammation in the bladder, inflammation or infection in the prostate gland, or pathology of the uterus; 2) focus on the idea of the pudendal nerve being entrapped and needing release; 3) focus on an autoimmune process; or 4) focus supposed on psychiatric problems deriving from a fear of sexual activity, a propensity toward malingering, or neurotic somatization. While all of these treatments have failed to resolve the problem of pelvic pain, an example of one of these approaches is shown in U.S. Pat. No. 2,478,786, which shows a prostate gland massaging implement. In the field of urology, prostate massage derives from the goal of expelling the prostate fluid suspected of containing inflammatory or infectious pathogens, for treating urinary frequency, urgency, dysuria and other related symptoms of bacterial or inflammatory prostatitis.

The approaches described above are based on a misunderstanding of the nature of most cases of pelvic pain commonly diagnosed as prostatitis. In recent years, evidence has emerged that a large majority of pelvic pain in men and women is related to muscle dysfunction and muscle related pain. Understanding most cases of prostatitis and pelvic pain as muscle related pain is an entirely new paradigm in urology. This new understanding sees chronic tension in the pelvic muscles producing trigger points, or taut bands within muscles either at the surface of the muscle, inside the muscle, in the belly or the attachment of the muscle. These trigger points are rather like mini-spasms in muscle that refer pain to remote sites, and when pressed routinely recreate a patient's symptoms. When pressed in a specific way these trigger points can release, often attended by a significant reduction or abatement in pain and dysfunction. Trigger points have been found to be strongly exacerbated with anxiety and other perpetuating factors. Trigger point release, particularly for trigger points located on the outside of the body has become a subspecialty within medicine. The inventor of the present invention, David Wise, Ph.D, along with his colleague and coauthor Rodney Anderson, M.D., professor of urology at Stanford University, previously described techniques for identifying and manipulating trigger points in their book *A Headache in the Pelvis: A New Understanding and Treatment for Prostatitis and Chronic Pelvic Pain Syndromes*, which was originally published by the National Center for Pelvic Pain Research in 2003, and is incorporated herein in its entirety by reference.

The research of Wise, Anderson and Sawyer has discovered that daily trigger point release along with other methods provides the most effective relief for pelvic pain. Many pelvic pain patients do not have access to professionals competent in internal trigger point release, are not able to afford the ongoing level of treatment, or are not able to find the time necessary to receive trigger point release. Thus, many patients have an urgent need for ongoing trigger point release related to pelvic pain that remains unmet due to the financial and time related problems existing in conventional professional treatment of internal trigger points and to the scarcity of internal trigger point practitioners. Previously known self-treatment apparatuses have proven ineffective for internal trigger point release because they were designed for other purposes and not for internal trigger point release. Previous apparatuses have not had the structural design to enable the patient to locate the often hard to find internal trigger points, nor have they provided any assistance in applying the appropriate pressure to release the trigger point and, importantly, at the same time to cause no bleeding tissue damage or perforation.

Accordingly, need remains for a method and apparatus by which patients could treat their own internal trigger points, accessed either vaginally or rectally using trigger point release techniques, without need for a visit to a physician or therapist.

SUMMARY OF THE INVENTION

In accordance with the invention, an apparatus and method for treating pelvic pain is provided. The apparatus includes a rod or wand having a handle attached to a straight portion at a first end of the wand and a pressure applicator attached to a second end of the wand, where a first curved portion is disposed between the straight portion of the wand and the second end of the wand. The first curved portion may be substantially semicircular, and may define an arc of approximately 180 degrees.

In some embodiments, the apparatus includes a wand having a second curved portion disposed between the first curved portion and the second end of the wand. The second curved portion of the wand may form an angle between 45 to 90 degrees with respect to the first curved portion of the wand, and the first curved portion of the wand and the second curved portion of the wand may cooperate to define a reverse curve.

In other embodiments, the apparatus includes a stop or platform that is adjustably disposed on the wand for adjustably restraining insertion of the pressure applicator into the body cavity. The stop includes a flange that is engageable with an external surface of the patient's body and a collar that is disposed on the wand. A positioning element may be provided on the collar of the stop, the positioning element moveable between an engaged position, where the positioning element engages the wand to restrain movement of the stop with respect to the wand, and a disengaged position, where the positioning element does not engage the wand and does not restrain movement of the stop with respect to the wand. Furthermore, the positioning element may have a threaded aperture formed through the collar and a set screw receivable within the threaded aperture for engagement with the wand.

In some other embodiments, the apparatus may include a pressure sensor and a display electrically connected to the pressure sensor to display a pressure value. The pressure sensor may be disposed in the pressure applicator, or the pressure sensor may be disposed in the straight portion of the wand.

In yet another embodiment, the pressure applicator is fabricated from an electrically conductive material, the wand fabricated from a non-electrically conductive material, and the apparatus includes an electrical stimulation unit electrically connected to the pressure applicator for supplying electrical current to the pressure applicator.

In the method of the present invention, a trigger point is located in the patient's pelvic floor. With a lubricated glove or condom covering the distal end, the patient inserts the apparatus either vaginally or rectally to allow contact of the pressure applicator of the apparatus with one or more trigger points located on the pelvic floor, and pressure is applied to the trigger point using the apparatus in order to release the trigger point.

In one embodiment, a hand-held internal therapeutic massager includes a rod having a first portion that defines a curve and a second portion that is substantially straight. The first portion of the rod is adapted to be inserted into a patient's body. A curvature of the curve defined by the first portion of the rod is sufficient to prevent the second portion of the rod from entering a patient's body. A handle is located on the second portion of the rod and a pressure applicator on the first portion of the rod is adapted to be inserted into the patient's body for engagement with a localized area of myofascial tissue. A vibratory device is disposed within the handle and is operable to generate vibrations. The vibrations generated by the vibratory device are conducted through the rod to the pressure applicator to the localized area of myofascial tissue.

BRIEF DESCRIPTION OF THE DRAWINGS

The description herein makes reference to the accompanying drawings, wherein like reference numerals refer to like parts throughout the several views, and wherein.

DETAILED DESCRIPTION OF THE PREFERRED EMBODIMENT

Figure 1:
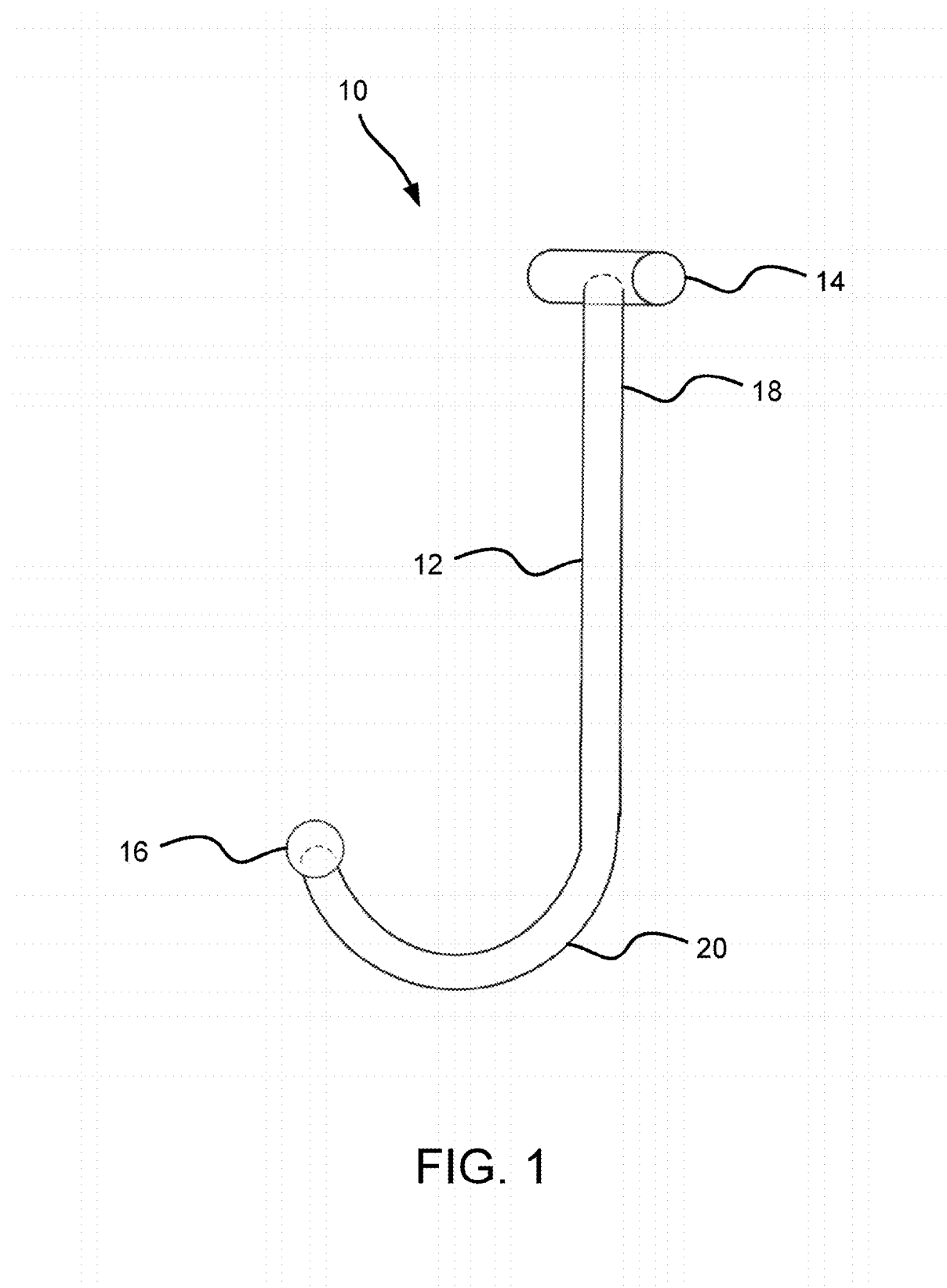
FIG. 1 is an illustration showing a first embodiment of the apparatus for treating pelvic pain according to the invention.
Figure 2:
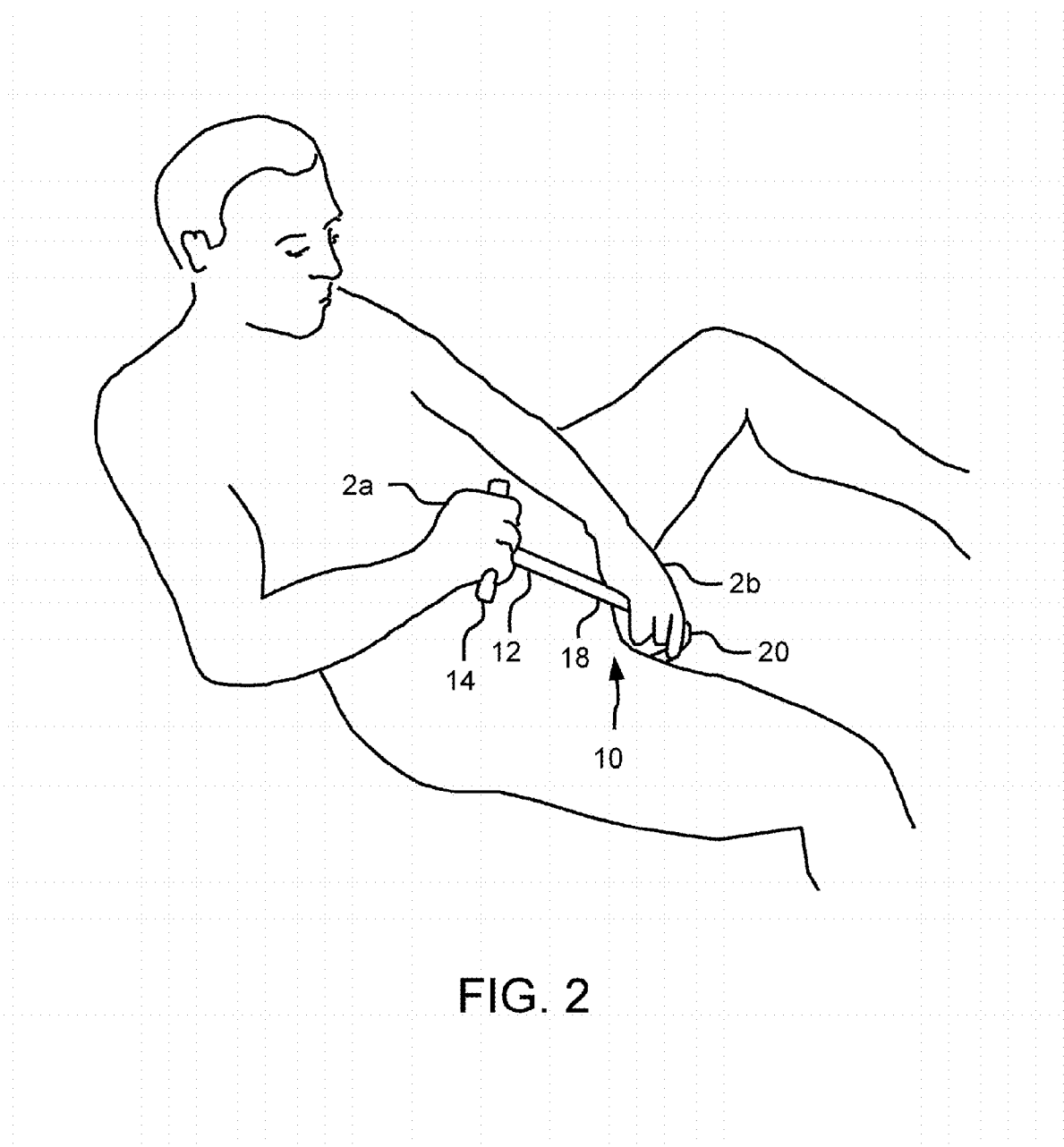
FIG. 2 is an illustration showing use of the first embodiment of the apparatus for treating pelvic pain according to the invention by a user.
Figure 3:
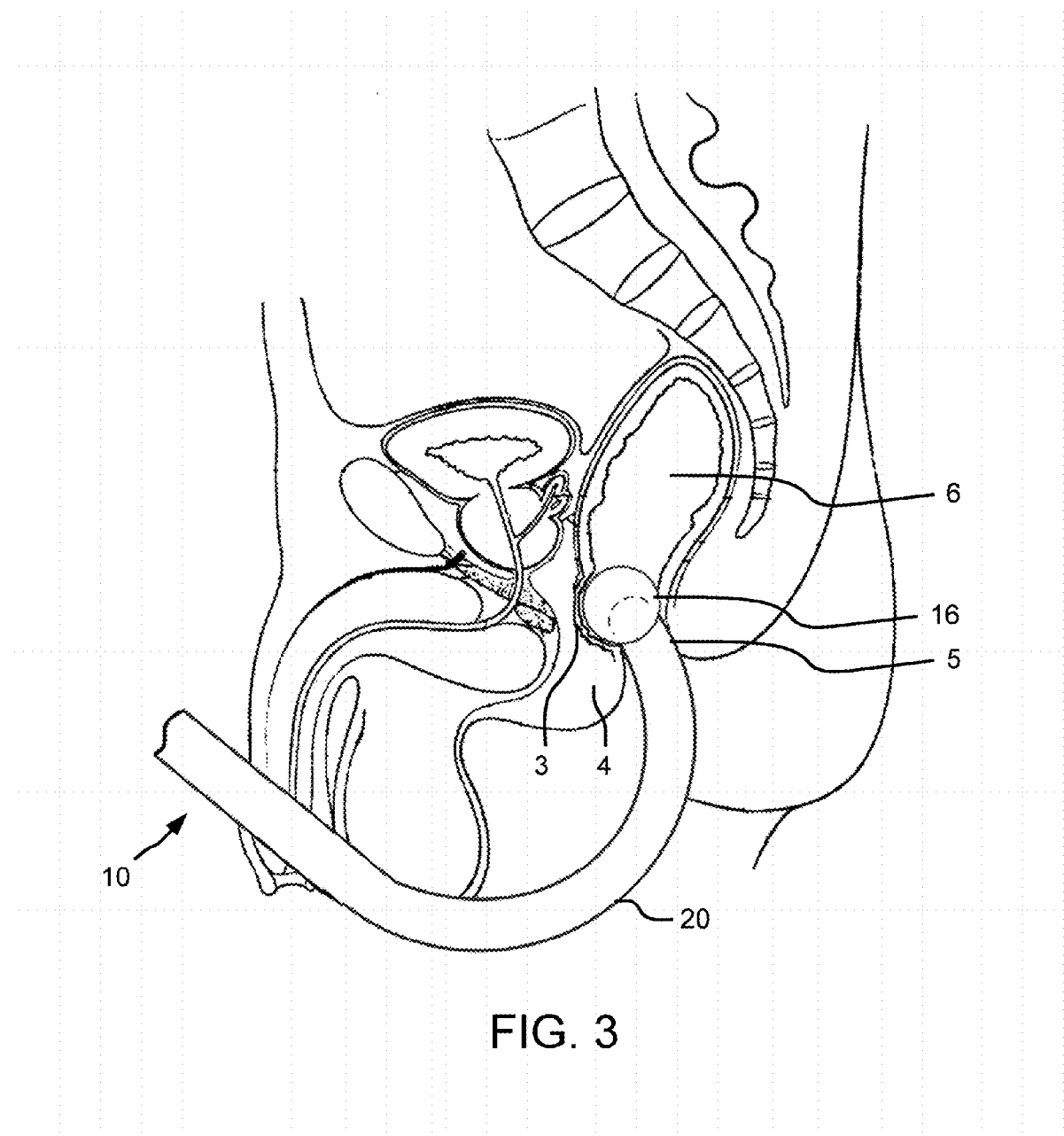
FIG. 3 is a partial cross section of the pelvis of the user showing engagement of the first embodiment of the apparatus for treating pelvic pain according to the invention with a myofascial trigger point.

Referring to FIGS. 1-3, there is shown an apparatus 10 in accordance with a first embodiment of the invention. The apparatus 10 includes a substantially j-shaped rod or wand 12, a handle member 14 connected to a first end of the wand 12, and a pressure applicator 16 connected to a second end of the wand 12. The handle member 14 and the pressure applicator 16 are connected to the wand 12 in any suitable conventional manner. The wand 12, the handle member 14, and the pressure applicator 16 may be fabricated from any suitable material, such as acrylic.

The wand 12 is a continuous member that has a straight portion 18 that extends from the handle member 14 for approximately ten inches before reaching a semicircular portion 20. The semicircular portion 20 defines an arc of approximately 180 degrees. However, it should be understood that the semicircular portion 20 need not be exactly semicircular, as long as it forms a generally u-shaped curve. The wand 12 may be either hollow or solid, as desired. The wand 12 is substantially slender member, having a diameter of, for example, three-eighths to one-half of an inch, such that the diameter of the wand 12 is large enough to provide sufficient strength to the apparatus 10 to allow the user to apply pressure using the pressure applicator 16 without undue deformation of the apparatus 10. Furthermore, this dimension is considered critical in that the diameter of the wand 12 must be small enough so that rectal insertion of the apparatus 10 does not induce defecation when the wand 12 is inserted rectally by a patient and so that the uncomfortable sensation caused by insertion of the wand 12 does not overpower the patient's ability to sense engagement of the pressure applicator 16 of the apparatus 10 with a trigger point 3.

The pressure applicator 16 is a substantially spherical or semi-spherical member adapted for engagement with trigger points 3 in the pelvic floor 4, as will be explained herein. The pressure applicator 16 is sized similarly to the tip of a human index finger (not shown) and is between nine-sixteenths of an inch in diameter and one and one-quarter inches in diameter. Preferably, the pressure applicator 16 is approximately eleven-sixteenths of an inch in diameter, which allows effective, safe pressure to be applied to the trigger point 3 to cause palpation of the trigger point. This range of dimensions is considered critical in that pressure applicators 16 in larger sizes, such as one inch and seven-eighths of an inch in diameter were tested and found to be unsuitable, as these pressure applicators 16 did not allow sufficient pressure to be applied to trigger points and made locating trigger points 3 difficult. Conversely, pressure applicators 16 in smaller sizes make palpating the trigger points 3 difficult and can cause excessive pressure to be applied. Although shown and described herein as substantially spherical, it should be understood that the pressure applicator 16 could be provided in other non-spherical shapes.

The apparatus 10 is a device used for patient's self-treatment of pelvic pain to deactivate trigger points inside their own pelvic floor 4 by inserting the device vaginally or rectally. More particularly, the apparatus 10 of the first embodiment allows the user to access anterior trigger points (trigger points toward the front of the pelvic floor 4, closer to the belly than the back) and perform ischemic compression (pressure that squeezes the blood out of what is being pressed) on anterior trigger points. It is meant to enable the user to do pressure release, strumming, stroking and other methods of trigger point release on these internal pelvic trigger points and areas of restriction, usually associated with pelvic floor 4 pain, urinary and defecatory dysfunction, on the muscles of the levator ani, coccygeus, pubococcygeus, obturator internus, piriformis and other internally accessed trigger points. The apparatus 10 may also be used to stretch restricted, shortened, chronically contracted internal pelvic muscle tissue so that it elongates and reduces in its pain, soreness and ability to refer these sensations. Trigger point release using the apparatus 10 involves finding the internal trigger point 3, which is described in detail in the 4th edition of *A Headache in the Pelvis* and in Travell and Simon's book, *A Trigger Point Therapy Manual*, holding it and pressing on it for a period of 30-90 seconds to release it and reduce it's ability to refer pain and symptoms to sites either remote from it or directly at the site of palpation.

The trigger point release aims to free the muscles in and around the pelvis of active trigger points 3 and to restore the muscles of the pelvic floor 4 to a flexible and lengthened state. The phenomenon of trigger points was introduced into medicine by Travell and Simon who published the first edition of *Myofascial Pain and Dysfunction: The Trigger Point Manual* in 1983, which was followed by a second edition in 1992. These books were the culmination of research that went back to 1942 when Dr. Travell published her first article on myofascial pain.

The concept of trigger points 3 is relatively new to medicine. Trigger points 3 are specifically defined herein as taut bands within a muscle, either at the surface of the muscle or inside the muscle, in the belly or at the attachment of the muscle. The trigger point 3 characteristically elicits a twitch response, detectable on ultrasound or via electromyograph (a machine that measures the electrical activity in a muscle in millionths of a volt), that can be felt by a trained practitioner while palpating the trigger point. When the trigger point is pressed, there is often a 'jump' response in the patient due to the reflexive reaction of the patient to the often exquisite tenderness of the trigger point upon palpation. Furthermore, the trigger point 3 characteristically refers pain/sensation to the site being pressed or to a site remote from it.

A trigger point 3 can be active or latent. An active trigger point 3 is considered able to refer pain and recreate that pain upon palpation when the patient comes in with a complaint of pain. A latent trigger point 3 has the capacity to be the source of pain (i.e., has the capacity to become an active one) and under certain circumstances, becomes active but generally the patient does not complain of symptoms from latent trigger points. Trigger points 3 are latent in many people. Trigger points 3 refer pain directly on the trigger point 3 site or to a remote site, which means that where pain is felt is often not where it actually is coming from. For instance, testicular pain is often referred from trigger points in the quadratus lumborum. This is not obvious and is anti-intuitive. This trigger point 3 can be around 8-10 inches away from the site of the discomfort. The internal muscles that contain trigger points 3 are often close to each other. The relationship between symptoms and the location of associated trigger points 3 is mostly found in Travell and Simon's textbooks.

Before using the apparatus 10, the patient receives instruction on the use of the apparatus 10 by a qualified physician, osteopath, nurse, physical therapist or other designated professional. After receiving competent instruction, the user may use the apparatus 10 while sitting down on a toilet seat, in the lithotomy position lying down with the legs parted, a position commonly used in the gynecologist office when a doctor does a digital vaginal examination, or while the user lies on his or her side. The apparatus 10 is held in front of the patient's body, with the straight portion 18 of the wand 12 extending along the torso of the user's body, toward the user's head, and the pressure applicator is inserted, for example, through the rectal opening 5 and into the rectal cavity 6. One of the user's hands 2*a* holds the handle 14 and pushes away from the user's body, while the other hand 2*b* holds the straight portion 18 of the wand 12 of the apparatus 10 near the semicircular portion 20 of the wand 12 and pulls it toward the body, thereby exerting pressure on the pressure applicator 16 of the apparatus 10 at a level of pressure of 1-12 lbs. as measured by the flexion of the straight rod at its tip as it engages the pelvic floor 4, in order to access and palpate anterior trigger points 3. A condom or rubber gloves are always placed over the tip of the apparatus 10 coming up 8-12 inches and sterile lubrication like KY Jelly® or Surgilube® is used to facilitate easy insertion and removal of the apparatus 10.

All of the internal trigger points 3 must be thoroughly evaluated and treated. When trigger points 3 are located, they are held with pressure release using the apparatus 10 which involves pressing on a trigger point 3 with constant pressure, usually for a period of 30-90 seconds. So that the patient may readily measure the elapsed time during trigger point release, the apparatus may include a timer (not shown) on the wand 12 or the handle member 14 of the apparatus 10.

Specific trigger points 3 in specific pelvic muscles tend to refer specific kinds of symptoms. For example, pain in the tip of the penis or the sense of urgency and frequency is typically created by active trigger points 3 in the anterior (front) portion of the levator ani muscle. When a patient uses the apparatus 10, knowledge of the relationship between symptoms and pelvic trigger points 3 is essential to be able to use the wand properly and instructions in the use of the apparatus 10 are part of its proper use and appropriate prescription by a physician or designated health care professional.

Figure 4:
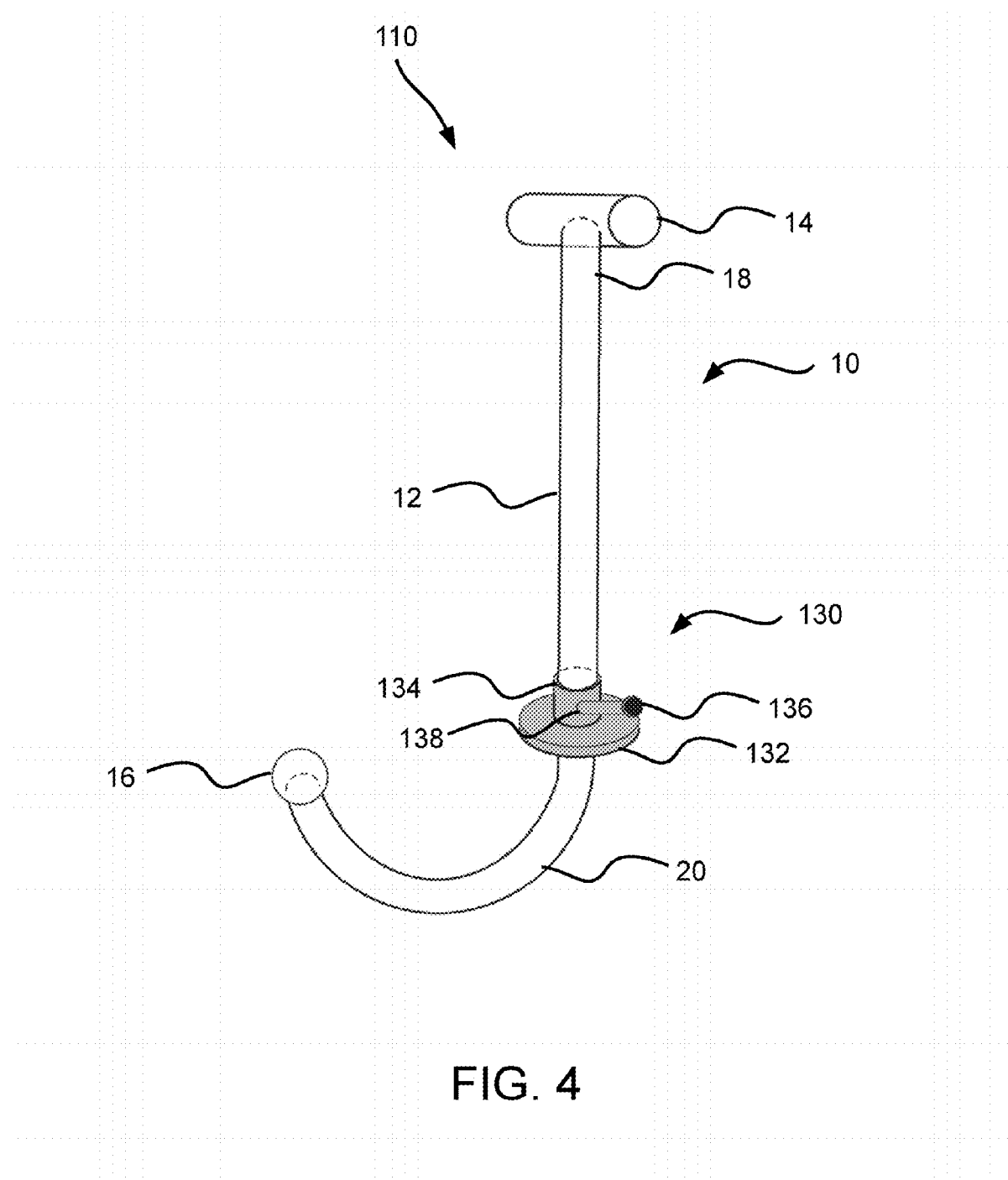
FIG. 4 is a side view of a second embodiment of the apparatus for treating pelvic pain according to the invention.

As shown in FIG. 4, an apparatus 110 according to a second embodiment of the invention includes all of the elements of the apparatus 10 of the first embodiment as well as an adjustable platform or stop 130 that is disposed on the wand 12. The adjustable stop 130 serves to limit the depth to which the user of the apparatus 110 may insert the pressure applicator 16 into the vagina or rectum.

This adjustable stop 130 allows the user to determine how far in to insert the wand 12 in order to accurately find and release internal pelvic floor 4 trigger points 3. At first, the position of the adjustable stop 130 on the wand 12 is adjusted by a therapist who has mapped out the user's internal trigger points 3 and who is teaching the user how to locate, self-treat and release her or his own trigger points 3. This is necessary since the locations of internal trigger points 3 are very difficult to discern, since patients are often incapable of accurately sensing the location of the pressure applicator 16 of the wand 12 once inserted. Thus, the user's doctor or therapist may determine the appropriate depth or depths at which the wand 12 needs to be inserted to access the trigger points 3 on which release will be performed by the patient. With the insertion depth fixed, the user may then identify the trigger point 3 location or locations more easily, since the range of motion of the pressure applicator 16 of the wand 12 is limited by engagement of the adjustable stop 130 with the exterior of the patient's body. Also, by using the adjustable stop 130, the maximum depth of insertion of the wand 12 is limited, thereby reducing the risk of patient injury, such as tissue bleeding, damage or internal organ perforation.

The adjustable stop 130 includes a flange 132 that extends radially outward from a collar 134 that is slidably disposed upon the wand 12. The flange 132 lies substantially perpendicular to the longitudinal axis of the wand 12, and is adapted to engage the exterior of the user's body to restrain the apparatus 110 against further insertion. The collar 134 is substantially tubular, and has an internal diameter complementary to the external diameter of the wand 12. A positioning element 136, such as a set screw, extends through a threaded aperture 138. The positioning element 136 moves between an engaged position, where the positioning element 136 engages the wand 12 to restrain movement of the adjustable stop 230 with respect to the wand 12, and a disengaged position, where the positioning element 136 does not engage the wand 12 and the adjustable stop 130 is not restrained from moving with respect to the wand 12. Thus, when the positioning element 136 of the adjustable stop 130 is in the disengaged position, the adjustable stop 130 may be slid along the wand 12 to any desired location on the straight portion 18 or the semicircular portion 20 of the wand 12. Then, when the adjustable stop 130 is in a desired position, the positioning element 136 may be moved to the engaged position to lock the adjustable stop 130 in the desired position.

Figure 5:
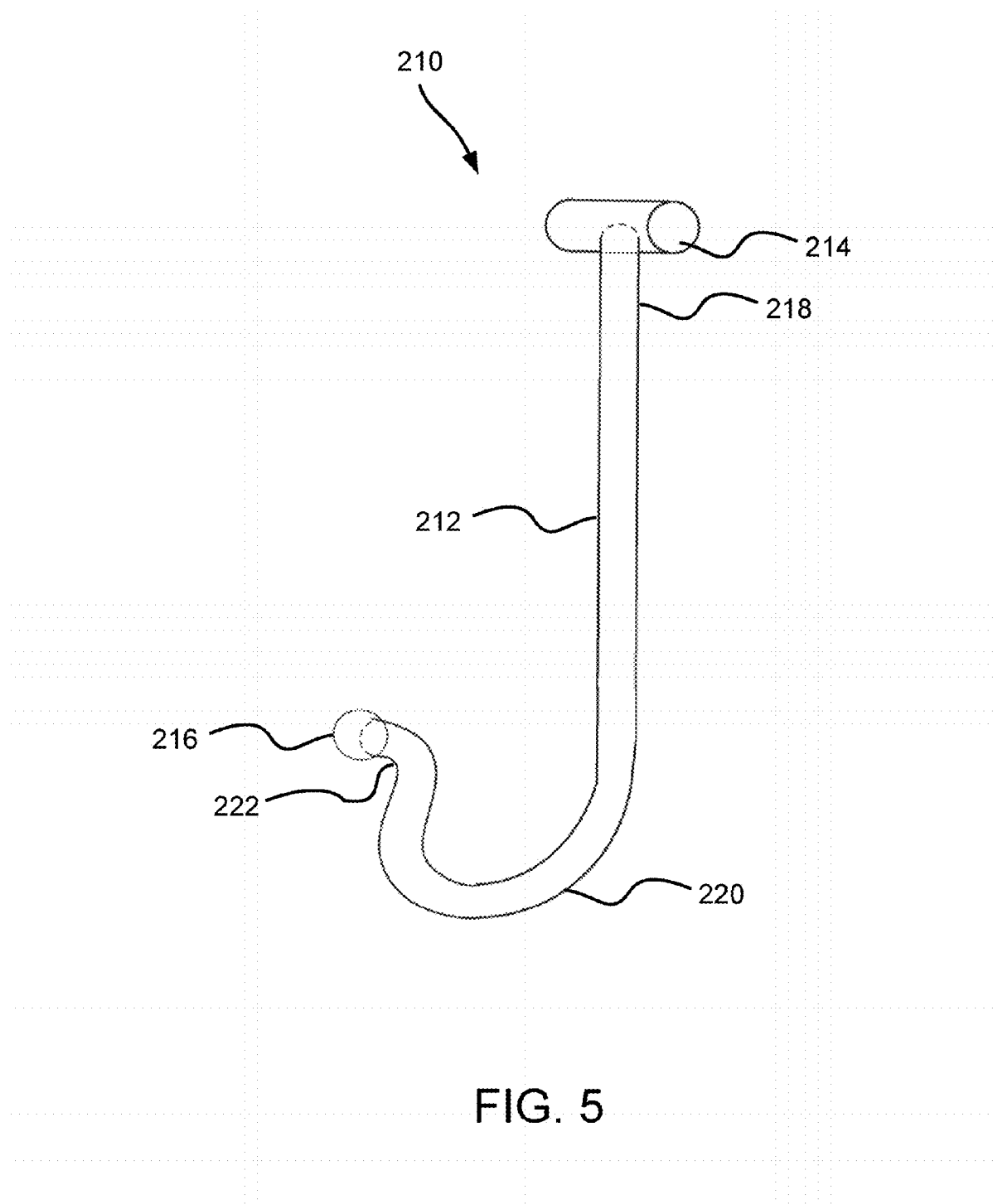
FIG. 5 is a side view of a third embodiment of the apparatus for treating pelvic pain according to the invention.

As shown in FIG. 5, an apparatus 210 according to a third embodiment of the invention includes a wand 212 having a primary curved portion 220 that is similar to the semicircular portion 20 of the apparatus 10 of the first embodiment, as well as a secondary curved portion 222 that is disposed between the primary curved portion 220 of the wand 212 and a pressure applicator 216 that is similar to the pressure applicator 16 of the apparatus 10 of the first embodiment. The primary curved portion 220 forms a generally u-shaped curve and may be substantially semicircular. The apparatus 210 also includes a handle 214 that is connected to a straight portion 218 of the wand 212. The handle 214 and the straight portion 218 are similar to the handle 14 and straight portion 18 of the apparatus 10 of the first embodiment.

The secondary curved portion 222 of the wand 212 is positioned along the wand so that it is disposed internally when the pressure applicator 216 is engaged with a trigger point 3. The secondary curved portion forms an angle between 45 to 90 degrees with respect to the primary curved portion 220, and the primary curved portion 220 and the secondary curved portion 222 may cooperate to define a reverse curve.

By providing the secondary curved portion 222 on the wand 212, the user may engage the pressure applicator 216 with posterior trigger points 3 (trigger points 3 located toward the back of the body, closer to the back than the belly), such as trigger points 3 on the coccygeus muscles, to perform ischemic compression, milking, or strumming of those trigger points 3.

Figure 6:
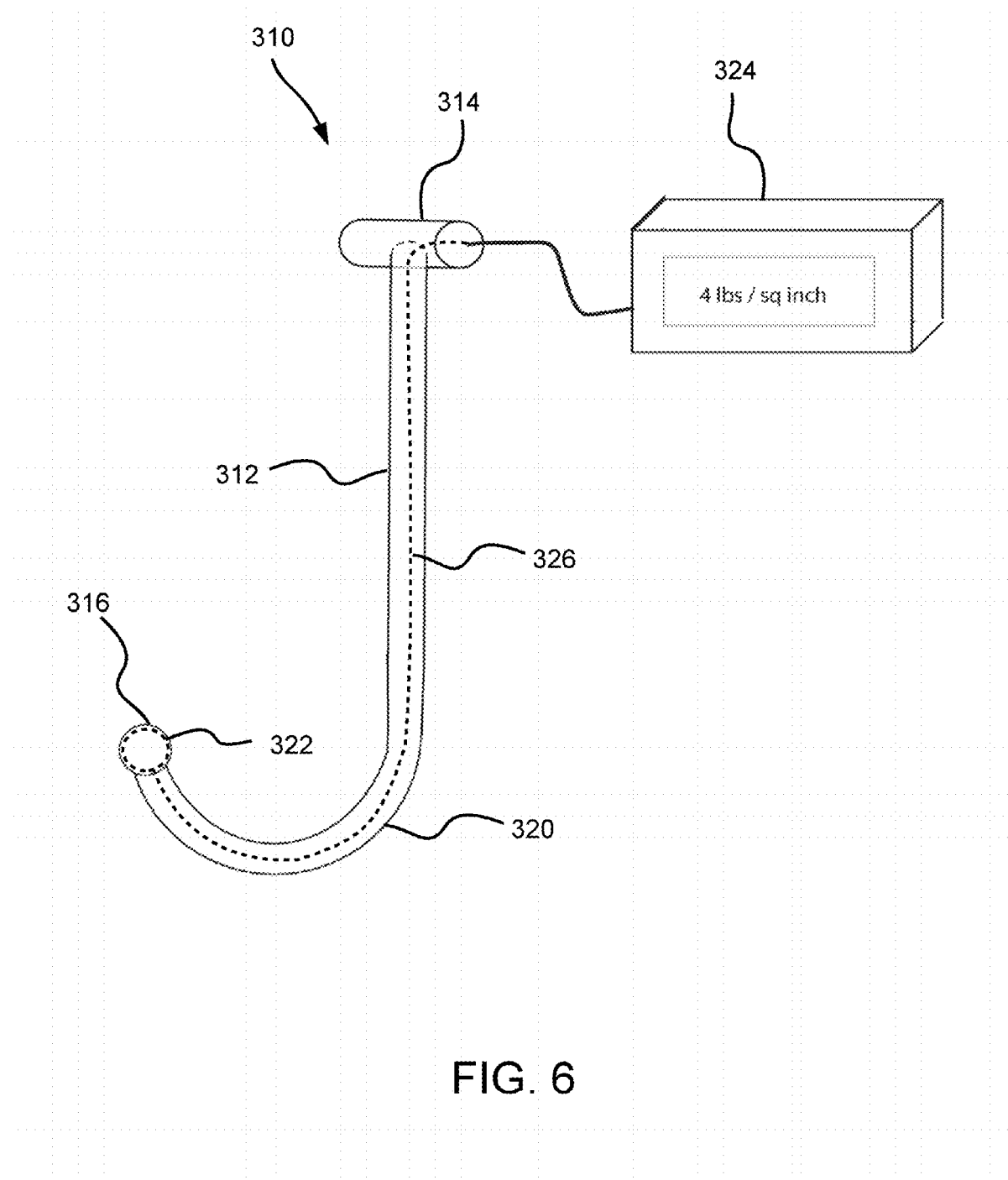
FIG. 6 is a side view of a fourth embodiment of the apparatus for treating pelvic pain according to the invention.

As shown in FIG. 6, an apparatus 310 according to a fourth embodiment of the invention includes a pressure sensor (algometer) 322 that is disposed within a pressure applicator 316. The wand 312, the handle 314, and the pressure applicator 316 are similar to the wand 12, the handle 14, and the pressure applicator 16 of the apparatus 10 of the first embodiment, respectively.

The pressure sensor 322 may be any conventional sensor operable to output an electrical signal corresponding to a sensed pressure value, and thus, the pressure sensor 322 is operable to detect the pressure applied to the trigger point 3 by the pressure applicator 316 of the wand. To provide information regarding the pressure applied by the pressure applicator 316 to the user, the pressure sensor 322 is electrically connected to a display 324 by a cable 326. The display 324 is a conventional digital or analog device operable to display a measured value corresponding to the measurement made by the pressure sensor 322 and thus allows the pressure applied by the pressure applicator 316 to be monitored by the patient during use of the apparatus 310. The display 324 may be disposed external to the wand 312 and the handle 314 in a separate housing, and the cable 326 may extend through the wand 312 and out of the handle 314 to the display 324. Alternatively, the display 324 may be disposed on the straight portion 318 of the wand 312 or on the handle 314. Provision of the pressure sensor 322 and the display 324 allows the patient to apply the amount of pressure to the trigger point 3 prescribed by the patient's doctor or therapist, thereby facilitating effective, safe trigger point 3 release.

Figure 7:
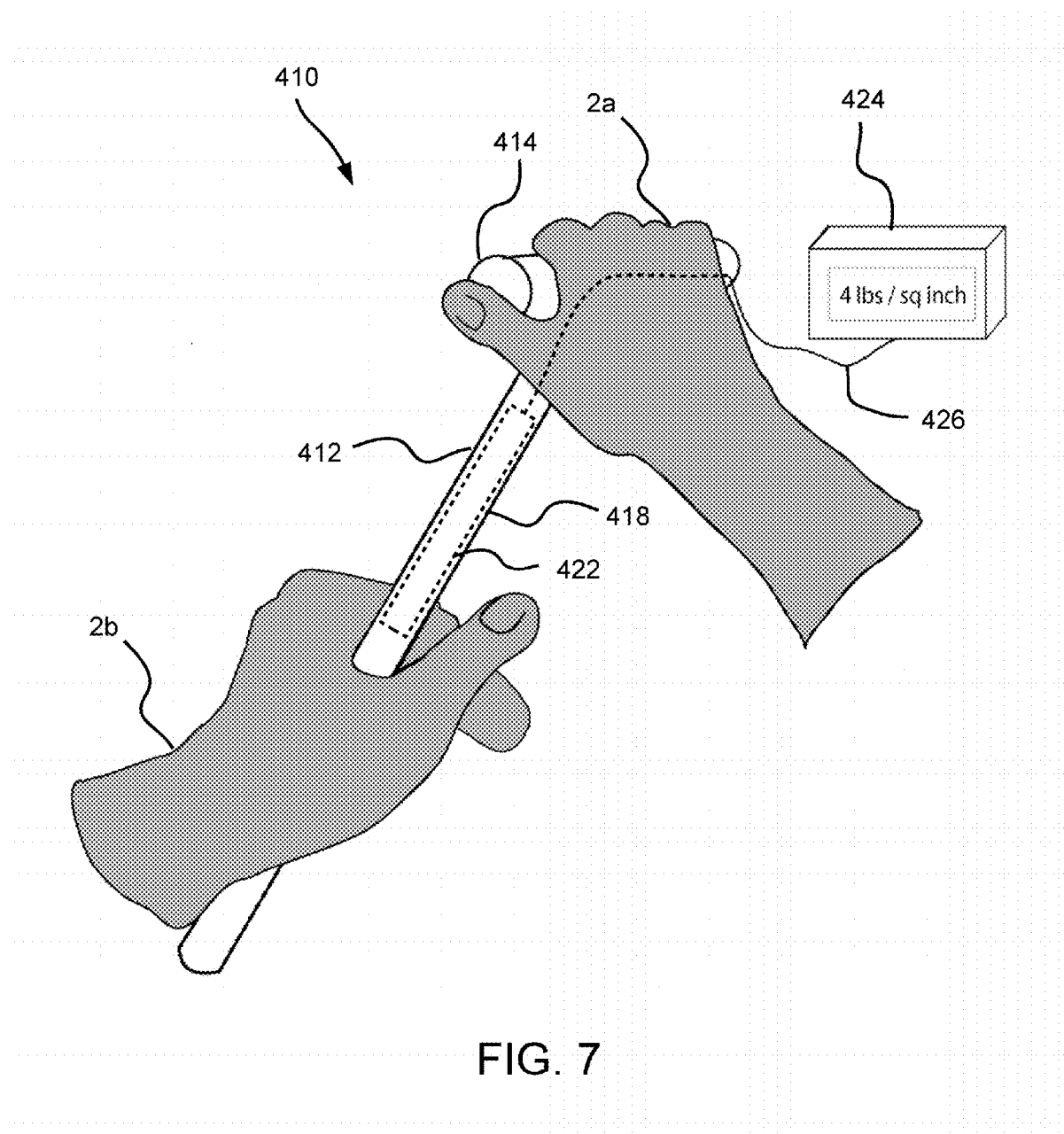
FIG. 7 is a side view of a fifth embodiment of the apparatus for treating pelvic pain according to the invention.

As shown in FIG. 7, an apparatus 410 according to a fifth embodiment of the invention includes a flexible pressure sensor 422 that is disposed within a straight portion 418 of a wand 412, adjacent to a handle 414. The flexible pressure sensor 422 is, for example, a flexible bend sensor that produces a changing output signal, such as resistance, as the degree of bending of the sensor occurs. Thus, the flexible pressure sensor 422 is an elongated body that is disposed within or embedded within the handle 414. The flexible pressure sensor 422 is electrically connected to a display 424 by a cable 426, which are similar to the display 324 and cable 326 of the apparatus 310 of the fourth embodiment, respectively. During use of the apparatus 410, the user places a first hand 2a on the handle 414 of the apparatus 410, and a second hand 2b on the straight portion 418 of the wand 412. Thus, when pressure is applied to the trigger point 3 using the pressure applicator 16 (not shown in FIG. 7), a deflection is induced in the straight portion 418 of the wand 412. This deflection is measured by the flexible pressure sensor 422 and, since it corresponds to the pressure applied by the pressure applicator 16, is converted to a pressure reading and output on the display 424.

Figure 8:
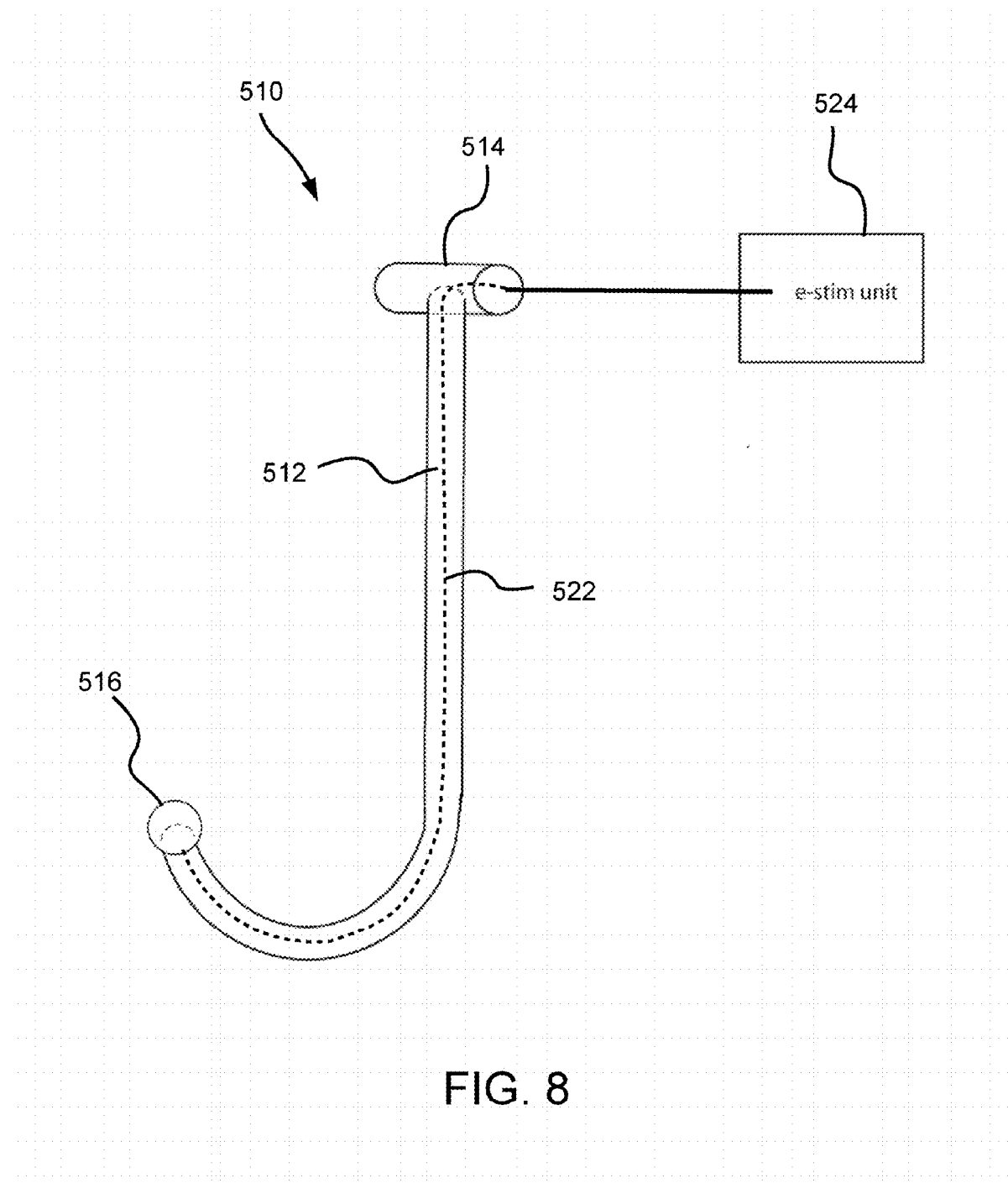
FIG. 8 is a side view of a sixth embodiment of the apparatus for treating pelvic pain according to the invention.

As shown in FIG. 8, an apparatus 510 according to a sixth embodiment of the invention includes an electrical stimulation unit 524. The wand 512, the handle 514, and the pressure applicator 516 are similar to the wand 12, the handle 14, and the pressure applicator 16 of the apparatus 10 of the first embodiment, respectively. However, the wand 512 of the apparatus 510 is fabricated from a non-electrically conductive material, such as acrylic, while the pressure applicator 516 is fabricated from an electrically conductive material. The electrical stimulation unit 524 is disposed external to the wand 512 and the handle 514, and is electrically connected to the pressure applicator 516 by a cable 522 that extends through the wand 512 and out of the handle 514. The electrical stimulation unit 524 is a conventional unit that is adapted to provide electrical current for electrical stimulation of muscles. Thus, the pressure applicator 516 may apply both pressure and electrical stimulation to the trigger point 3 using the electrical stimulation unit 524.

Figure 9:
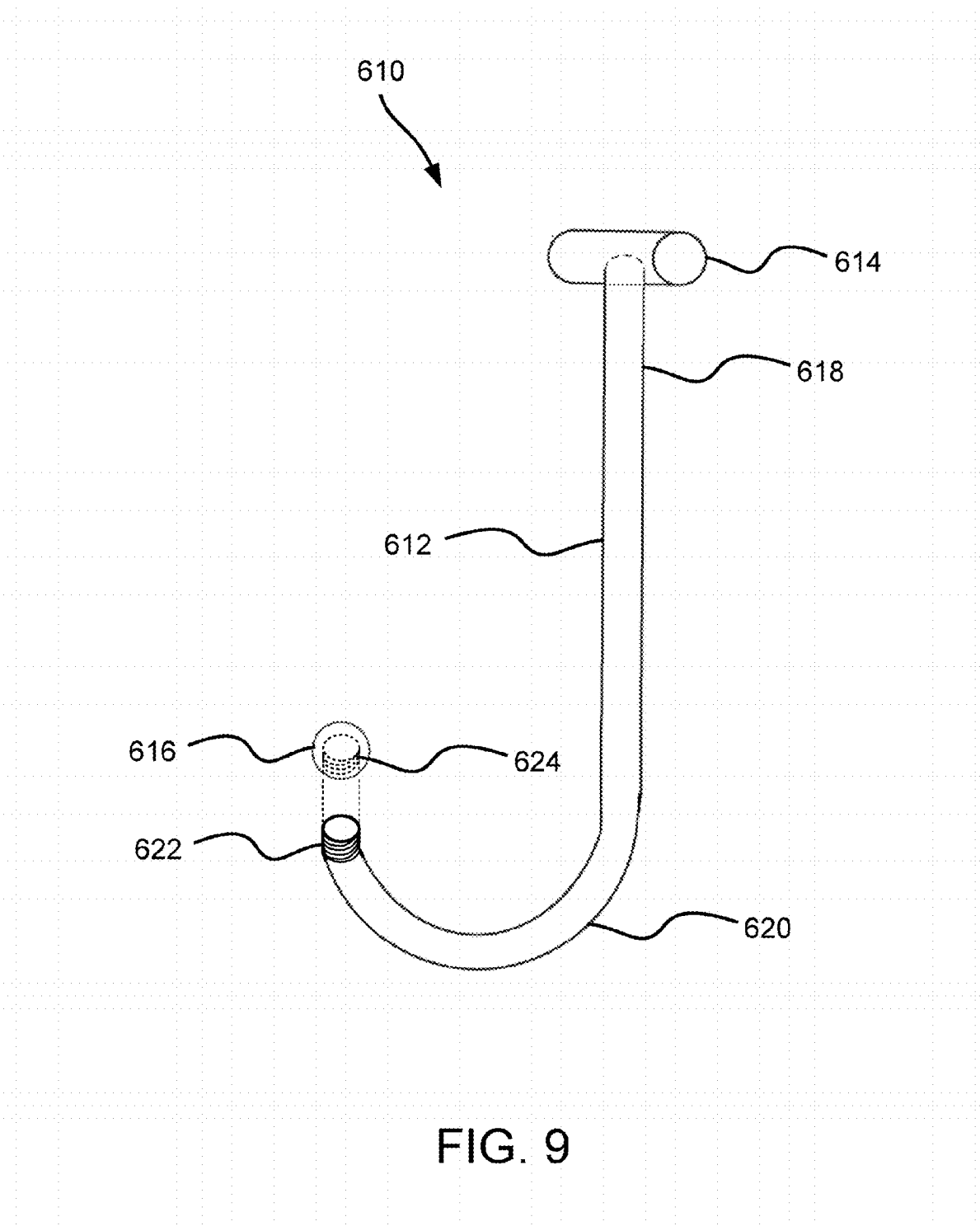
FIG. 9 is a side view of a seventh embodiment of the apparatus for treating pelvic pain according to the invention.

As shown in FIG. 9, an apparatus 610 according to a seventh embodiment of the invention includes a removable pressure applicator 616. The wand 612, the handle 614, and the pressure applicator 616 are similar to the wand 12, the handle 14, and the pressure applicator 16 of the apparatus 10 of the first embodiment, respectively. However, a threaded portion 622 is provided at the distal end of the curved portion 620 of the wand 612, and a threaded recess 624 is provided on the pressure applicator 616. Thus the pressure applicator 616 may be threadedly connected and disconnected from the wand 612. By providing a selectively detachable pressure applicator 616, a plurality of pressure applicators 616 may be provided having various diameters ranging between nine-sixteenth of one inch in diameter and one and one-quarter inches in diameter. Thus, the patient may utilize the apparatus with a larger diameter pressure applicator 616 when the trigger point 3 is near the surface, and may utilize a smaller diameter pressure applicator 616 when the trigger point 3 is located deep within the patient's muscles.

Figure 10:
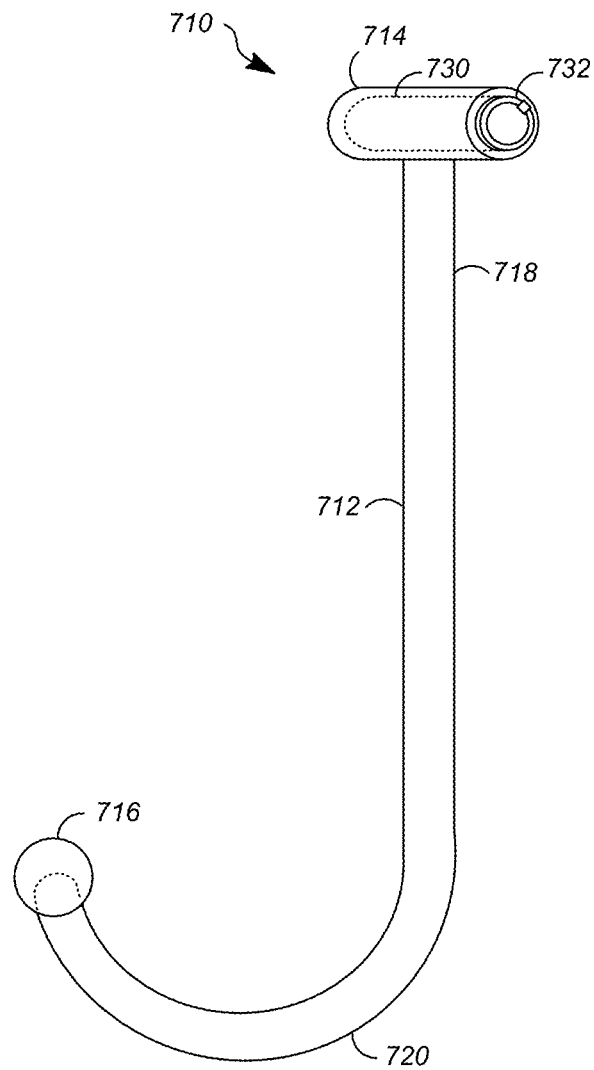
FIG. 10 is a side view of an eighth embodiment of the apparatus for treating pelvic pain according to the invention.

As shown in FIG. 10, an apparatus 710 according to an eighth embodiment of the invention includes a vibratory device 730. The wand 712, the handle 714, and the pressure applicator 716 are similar to the wand 12, the handle 14, and the pressure applicator 16 of the apparatus 10 of the first embodiment, respectively. However, the vibratory device 730 is disposed within a recess that is formed in the handle 714, which is located at one end of the wand 712 opposite the pressure applicator 716, with the handle 714 extending generally transverse to the wand 712. The vibratory device 730 is operable to generate vibrations. The vibrations generated by the vibratory device 730 can be of various frequencies and intensities.

In the illustrated example, the vibratory device 730 includes one or more control switches 732 to control the frequency (speed) and/or intensity of vibration generated by the vibratory device 730. For example, an intensity of the vibrations generated by the vibratory device 730 can be infinitely adjustable or discretely adjustable between a minimum intensity value and a maximum intensity value using the one or more control switches 732. Furthermore, for example, a frequency (speed) of the vibrations generated by the vibratory device 730 can be infinitely adjustable or discretely adjustable between a minimum frequency value and a maximum frequency value using the one or more control switches. In one implementation, the vibratory device has a frequency that is adjustable from 0 to 180 cycles per second. As will be explained, adjustment of the vibratory device 730 changes the motion induced at the pressure applicator 16, ranging from subtle vibration to a wobbling motion that mimics the manual strumming technique trigger point release therapy.

In one implementation, the vibratory device includes an electromagnetic motor that produces vibration as a function of rotation, for example, using an eccentric weight. In another implementation, vibration is produced using a piezoelectric transducer or an ultrasonic device, such as an ultrasonic motor, which produce vibration in response to an electrical signal (waveform) that controls the intensity and the frequency of the vibration that is generated, where the electrical signal is generated by a control circuit of the vibratory device 730. The vibratory device 730 can be internally-powered, such as by batteries, or can be externally powered, by connection, such as a wired electrical connection, to an external power source.

In operation, the vibratory device 730 produces vibrations that are conducted along the wand 712, which can be a solid rod formed of a resilient material, and through the pressure applicator 716 to deliver gentle vibration to a treatment site, such as a myofascial trigger point of on the patient's pelvic floor, which is access via a rectal cavity or a vaginal cavity of the patient, as previously described. By locating the vibratory device 730 outside of the patient's rectal cavity or vaginal cavity, electrical components are not placed within the patient. Furthermore, the remote location of the vibratory device 730 attenuates the vibration to prevent overstimulation of the treatment site. In addition, as a result of the location of the vibratory device being within or adjacent to the handle, in combination with the curved shape of the wand 712, the vibration generated by the vibratory device wand 712 can induce a wobbling motion at the pressure applicator 716, especially when low frequency, large amplitude vibrations are generated by the vibratory device 730. This wobble mechanically mimics the method of manual strumming in trigger point release, by which the pressure applicator 716 is moved across the fibers of a muscle, and by adjusting the vibration produced by the vibratory device 730, a finer or rougher wobble can be induced at the pressure applicator 716.

Figure 11:
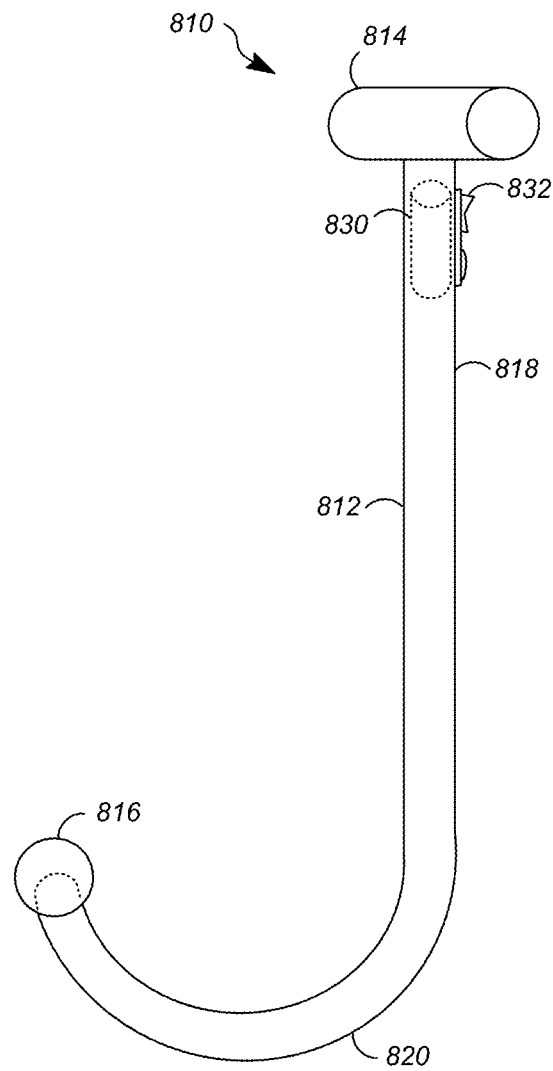
FIG. 11 is a side view of a ninth embodiment of the apparatus for treating pelvic pain according to the invention.

As shown in FIG. 11, an apparatus 810 according to an ninth embodiment of the invention includes a vibratory device 830 and one or more control switches 832. The wand 812, the handle 814, and the pressure applicator 816 are similar to the wand 12, the handle 14, and the pressure applicator 16 of the apparatus 10 of the first embodiment, respectively. The vibratory device 830 and the one or more control switches 832 are similar to the vibratory device 830 and the one or more control switches 832. However, the vibratory device 830 is disposed within a recess that is formed in the wand 812. The vibratory device 830 is disposed within the wand 812 adjacent to an end of the wand 812, adjacent to the handle 814, and spaced apart from the curved portion of the wand 812 and the pressure applicator 816. The use and effects of the apparatus 810 are similar to those of the apparatus 710.

The apparatus 710 of FIG. 10 and the apparatus 810 of FIG. 11 can both be utilized in conjunction with features previously described with respect to other embodiments. For example, the stop 130 of the apparatus 110 can be incorporated with either of the apparatus 710 or the apparatus 810 such that the stop 130 is disposed between the vibratory device 730, 830 and the pressure applicator 716, 816, and prevents the vibratory device 730, 830 from entering the patient's vaginal cavity or rectal cavity.

Figure 12:
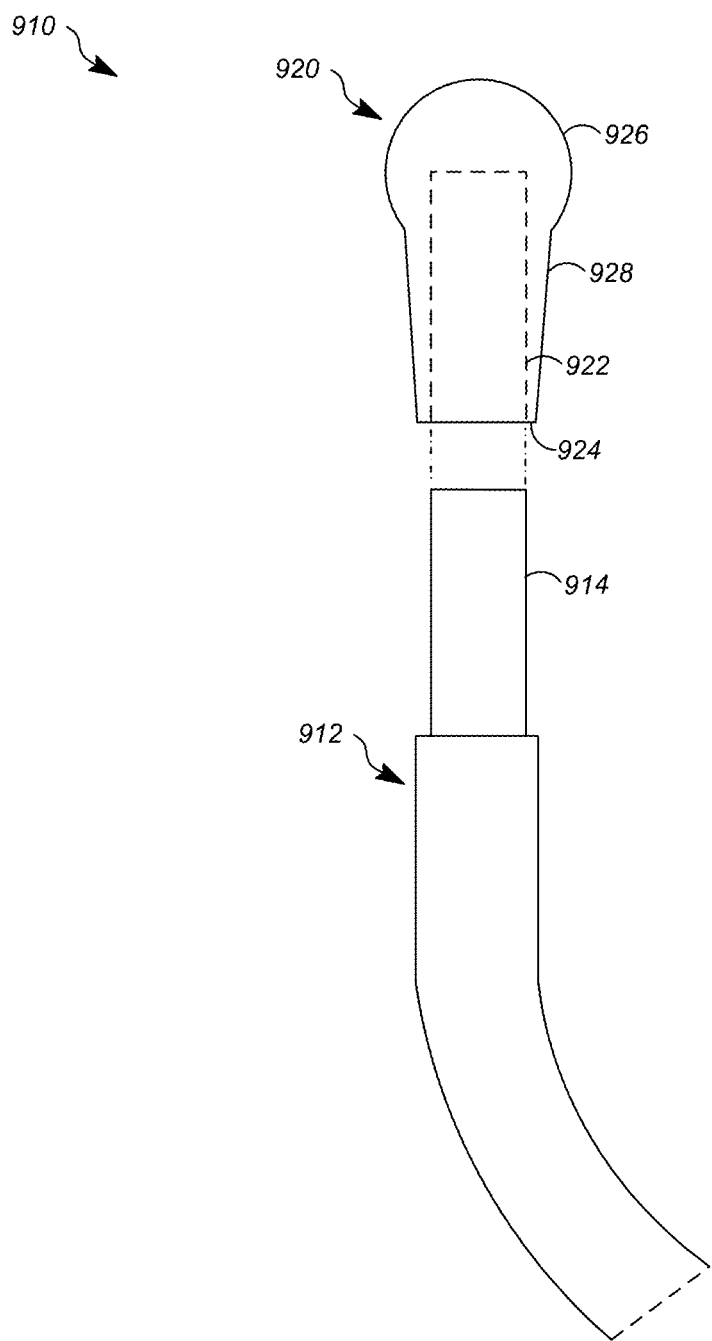
FIG. 12 is a side view of a tenth embodiment of the apparatus for treating pelvic pain according to the invention.

FIG. 12 is a side view of a tenth embodiment of an apparatus 910 for treating pelvic pain according to the invention. The apparatus 910 includes a wand 912, which is as described in previous embodiments and can include or be used with the various features shown in previous embodiments. A pressure applicator 920 is located at one end of the wand 912. In the illustrated example, a narrowed end 914 of the wand is received within a bore 922 defined by the pressure applicator, and a nominal outer diameter of the wand 912 is wider than the narrowed end and is substantially the same as an outside diameter of a base 924 of the pressure applicator 920. At least part of the end portion 926 of the pressure applicator has a substantially spherical shape, which changes to a frustroconical shape at a transition section 928 that provides a gradual change in diameter for the pressure applicator 920, which can aid insertion and removal of the pressure applicator, thus improving patient comfort.

In one implementation, the wand 912 and the pressure applicator 920 are formed separately. The pressure applicator 920 being formed from a low durometer, bio-compatible thermoplastic elastomer material, with the end portion having a diameter of about 0.75 inches, the base having a diameter of about 0.5 inches, and a length of about 1.375 inches. The wand can be formed from a material such as ultem, and have a diameter of about 0.375 inches along the narrowed end, and a diameter of about 0.5 inches elsewhere.

Use of the apparatuses of the second through ninth embodiments is performed in substantially the same manner as described in connection with the first embodiment. Of course, it should be understood that the features of the above embodiments may be combined. For example, an apparatus could be provided having the adjustable stop 130 according to the second embodiment, the primary curved portion 220 and the secondary curved portion 222 as demonstrated in the third embodiment, as well as the flexible pressure sensor 422 and the display 424 of the fourth embodiment.

While the invention has been described in connection with what is presently considered to be the most practical and preferred embodiment, it is to be understood that the invention is not to be limited to the disclosed embodiments, but to the contrary, it is intended to cover various modifications or equivalent arrangements included within the spirit and scope of the appended claims. The scope is to be accorded the broadest interpretation so as to encompass all such modifications and equivalent structures as is permitted under the law.

What is claimed is:

1. A hand-held internal therapeutic massager device for manually providing direct pressure to a localized area of myofascial tissue, the hand-held internal therapeutic massager device comprising:
    a rod that is a one-piece, non-hollow member that is fabricated from a non-electrically conductive material, the rod having a first portion that defines a curve and a second portion that is substantially straight, wherein the first portion of the rod is adapted to be inserted into a patient's body and a curvature of the curve defined by the first portion of the rod is sufficient to prevent the second portion of the rod from entering a patient's body;
    a handle located on the second portion of the rod;
    a pressure applicator that is located on the first portion of the rod and is adapted to be inserted into the patient's body for engagement with the localized area of myofascial tissue; and
    a stop that is slidably disposed on the rod to adjust an insertion depth of the pressure applicator with respect to the patient's body cavity, the stop having an opening that extends through the stop and a surface that extends outward from the opening, wherein the rod passes through the opening and the stop is engageable with an external surface of the patient's body, wherein the stop includes a positioning element that is moveable between an engaged position, where the positioning element engages the rod to restrain movement of the stop with respect to the rod, and a disengaged position, where the positioning element does not engage the rod and does not restrain movement of the stop with respect to the rod; and
    a vibratory device that is disposed within the handle and is operable to generate vibrations, wherein the vibrations generated by the vibratory device are conducted through the rod to the pressure applicator to the localized area of myofasical tissue, wherein the stop is disposed between the vibratory device and the pressure applicator.

2. The hand-held internal therapeutic massager device of claim 1, wherein the pressure applicator is at least semi-spherical and is sized such that it can be inserted into the patient's body.

3. The hand-held internal therapeutic massager device of claim 1, wherein the pressure applicator is substantially spherical and is sized such that it can be inserted into the patient's body.

4. The hand-held internal therapeutic massager device of claim 1, wherein the pressure applicator is sized such that it can be inserted into the patient's body and the rod has a diameter that is smaller than the diameter of the pressure applicator.

5. The hand-held internal therapeutic massager device of claim 1, wherein the rod is sized such that it can be inserted into the patient's body and the pressure applicator has a diameter that is larger than the diameter of the rod.

6. The hand-held internal therapeutic massager device of claim 1, wherein the rod has a diameter that is between three eighths of an inch and one half of an inch and the pressure applicator is between nine-sixteenths of an inch and one and one quarter inches in diameter.

7. The hand-held internal therapeutic massager device of claim 1, wherein the curve defined by the first portion of the rod is substantially u-shaped.

8. The hand-held internal therapeutic massager device of claim 1, wherein the first portion of the rod defines a substantially circular curve.

9. The hand-held internal therapeutic massager device of claim 1, wherein the first portion of the rod defines a curve of one hundred and eighty degrees.

10. The hand-held internal therapeutic massager device of claim 1, wherein the vibratory device has at least one of an adjustable intensity or an adjustable frequency.

11. A hand-held internal therapeutic massager device for manually providing direct pressure to a localized area of myofascial tissue, the hand-held internal therapeutic massager device comprising:
    a rod that is fabricated from a non-electrically conductive material, the rod having a first portion that defines a curve and a second portion that is substantially straight, wherein the rod has a diameter that is between three eighths of an inch and one half of an inch;
    a handle located on the second portion of the rod;
    a pressure applicator located on the first portion of the rod, wherein the pressure applicator is between nine-sixteenths of an inch and one and one quarter inches in diameter and is adapted to be inserted into a patient's body cavity for engagement with the localized area of myofascial tissue;
    a stop that is slidably disposed on the rod to adjust an insertion depth of the pressure applicator with respect to the patient's body cavity, the stop having an opening that extends through the stop and a surface that extends outward from the opening, wherein the rod passes through the opening and the stop is engageable with an external surface of the patient's body, wherein the stop includes a positioning element that is moveable between an engaged position, where the positioning element engages the rod to restrain movement of the stop with respect to the rod, and a disengaged position, where the positioning element does not engage the rod and does not restrain movement of the stop with respect to the rod; and
    a vibratory device that is disposed within the handle and is operable to generate vibrations, wherein the vibrations generated by the vibratory device are conducted through the rod to the pressure applicator to the localized area of myofasical tissue, wherein the stop is disposed between the vibratory device and the pressure applicator.

12. The hand-held internal therapeutic massager device of claim 11, wherein the rod is a solid, continuous member one-piece, non-hollow member that extends continuously from the handle to the pressure applicator.

13. The hand-held internal therapeutic massager device of claim 11, wherein the second portion of the rod is approximately ten inches long.

14. The hand-held internal therapeutic massager device of claim 11, wherein the first portion of the rod defines at least one of a u-shaped curve, a substantially circular curve, or a curve of one hundred and eighty degrees.

15. The hand-held internal therapeutic massager device of claim 11, wherein the pressure applicator is substantially spherical.

16. The hand-held internal therapeutic massager device of claim 11, wherein the pressure applicator is at least semi-spherical.

17. The hand-held internal therapeutic massager device of claim 11, wherein the positioning element is a threaded element that is received in a threaded aperture of the stop.

18. A hand-held internal therapeutic massager device for manually providing direct pressure to a localized area of myofascial tissue, the hand-held internal therapeutic massager device comprising:

a rod that is a one-piece, non-hollow member that is fabricated from a non-electrically conductive material, the rod having a first portion that defines a curve and a second portion that is substantially straight, wherein the first portion of the rod is adapted to be inserted into a patient's body and a curvature of the curve defined by the first portion of the rod is sufficient to prevent the second portion of the rod from entering a patient's body;

a handle located on the second portion of the rod;

a pressure applicator that is located on the first portion of the rod and is adapted to be inserted into the patient's body for engagement with the localized area of myofascial tissue;

a stop that is slidably disposed on the rod to adjust an insertion depth of the pressure applicator with respect to the patient's body cavity, the stop having an opening that extends through the stop and a surface that extends outward from the opening, wherein the rod passes through the opening and the stop is engageable with an external surface of the patient's body, wherein the stop includes a positioning element that is moveable between an engaged position, where the positioning element engages the rod to restrain movement of the stop with respect to the rod, and a disengaged position, where the positioning element does not engage the rod and does not restrain movement of the stop with respect to the rod; and a vibratory device that is disposed within the second portion of the rod and is operable to generate vibrations, wherein the vibrations generated by the vibratory device are conducted through the rod to the pressure applicator to the localized area of myofasical tissue, wherein the stop is disposed between the vibratory device and the pressure applicator.

19. The hand-held internal therapeutic massager device of claim 18, wherein the vibratory device is located adjacent to the handle.

* * * * *